US012790627B2

(12) United States Patent
Oguma et al.

(10) Patent No.: US 12,790,627 B2
(45) Date of Patent: Nov. 10, 2026

(54) METHOD FOR PRODUCING POLYHYDROXYALKANOIC ACID AND USE OF SAME

(71) Applicant: KANEKA CORPORATION, Osaka (JP)

(72) Inventors: Toshi Oguma, Takasago (JP); Masaru Hirano, Takasago (JP)

(73) Assignee: KANEKA CORPORATION, Osaka (JP)

(*) Notice: Subject to any disclaimer, the term of this patent is extended or adjusted under 35 U.S.C. 154(b) by 259 days.

(21) Appl. No.: 18/681,441

(22) PCT Filed: Jul. 8, 2022

(86) PCT No.: PCT/JP2022/027042

§ 371 (c)(1),
(2) Date: Feb. 5, 2024

(87) PCT Pub. No.: WO2023/021878

PCT Pub. Date: Feb. 23, 2023

(65) Prior Publication Data

US 2024/0336942 A1 Oct. 10, 2024

(30) Foreign Application Priority Data

Aug. 19, 2021 (JP) ................................ 2021-134285

(51) Int. Cl.
*C12P 7/42* (2006.01)
*C12N 1/20* (2006.01)

(52) U.S. Cl.
CPC .................. *C12P 7/42* (2013.01); *C12N 1/20* (2013.01); *C12N 2500/05* (2013.01)

(58) Field of Classification Search
CPC .... C12P 7/42; C12P 7/625; C12P 1/00; C12N 1/20
See application file for complete search history.

(56) References Cited

U.S. PATENT DOCUMENTS

| | | | |
|---|---|---|---|
| 5,627,276 A | 5/1997 | Greer | |
| 2005/0196827 A1 | 9/2005 | Osakada et al. | |
| 2005/0222373 A1 | 10/2005 | Kinoshita et al. | |
| 2006/0084161 A1 | 4/2006 | Yanagita et al. | |
| 2006/0127998 A1* | 6/2006 | Ogawa .................. | C08G 63/90 435/135 |
| 2007/0072276 A1 | 3/2007 | Chen | |
| 2022/0340710 A1 | 10/2022 | Nishinaka et al. | |

FOREIGN PATENT DOCUMENTS

| | | | |
|---|---|---|---|
| CN | 111019108 | A | 4/2020 |
| EP | 3 960 868 | A1 | 3/2022 |
| JP | 8-502415 | A | 3/1996 |
| JP | 2007-524345 | A | 8/2007 |
| JP | 2012-115145 | A | 6/2012 |
| WO | WO 99/05207 | A1 | 2/1999 |
| WO | WO 2004/029266 | A1 | 4/2004 |
| WO | WO 2004/065608 | A1 | 8/2004 |
| WO | WO 2005/049692 | A1 | 6/2005 |
| WO | WO 2005/085461 | A1 | 9/2005 |
| WO | WO 2008/010296 | A1 | 1/2008 |
| WO | WO 2010/116681 | A1 | 10/2010 |
| WO | WO 2015/015395 | A1 | 2/2015 |
| WO | WO 2020/218565 | A1 | 10/2020 |
| WO | WO 2021/085120 | A1 | 5/2021 |
| WO | WO 2021/085534 | A1 | 5/2021 |
| WO | WO 2022/015539 | A1 | 1/2022 |

OTHER PUBLICATIONS

International Preliminary Report on Patentability and Written Opinion issued Feb. 13, 2024 in PCT/JP2022/027042 (with English translation), 10 pages.
International Search Report issued Sep. 27, 2022 in PCT/JP2022/027042 (with English translation), 4 pages.
Yasotha et al., Recovery of medium-chain-length polyhydroxyalkanoates (PHAs) through enzymatic digestion treatments and ultrafiltration, Biochem. Eng. J. 30, 2006, 260-68. (Year: 2006).
International Search Report issued Nov. 30, 2021 in PCT/JP2021/036938 (with English Translation), 6 pages.
Written Opinion of the International Searching Authority issued Nov. 30, 2021 in PCT/JP2021/036938 (with English Translation), 8 pages.
Jiang et al., "Feasibility study of an alkaline-based chemical treatment for the purification of polyhydroxybutyrate produced by a mixed enriched culture", AMB Express, vol. 5, No. 5, 2015, pp. 1-13.
Extended European Search Report issued Jun. 11, 2025 in European patent Application No. 21897508.4, 8 pages.
Ramsay et al., Extraction of poly-3-hydroxybutyrate using chlorinated solvents, Biotechnol. Lett. 8, 1994, 589-94. (Year: 1994).
Yu et al., Characterization of low molecular weight poly(beta-hydroxybutyrate)s from alkaline and acid hydrolysis, Polymer 41, 2000, 1087-98.

* cited by examiner

*Primary Examiner* — Tekchand Saidha
(74) *Attorney, Agent, or Firm* — Oblon, McClelland, Maier & Neustadt, L.L.P.

(57) ABSTRACT

It is an object of an embodiment of the present invention to provide an industrially easily applicable technology for reducing a viscosity of a culture solution, in order to collect a polyhydroxyalkanoate from a polyhydroxyalkanoate-producing microorganism. The object is attained by providing a method for producing a polyhydroxyalkanoate, including the following steps (a) and (b): (a) maintaining a culture solution at 40° C. to 80° C., the culture solution including microbial cells containing the polyhydroxyalkanoate; and (b) adding an oxidizer to the culture solution obtained in the step (a), adjusting a pH of the culture solution to 10.5 to 13.0, and maintaining the culture solution at 30° C. to 75° C.

13 Claims, No Drawings

METHOD FOR PRODUCING POLYHYDROXYALKANOIC ACID AND USE OF SAME

CROSS-REFERENCE TO RELATED APPLICATIONS

The present application is a 35 U.S.C. § 371 national stage patent application of International patent application PCT/JP2022/027042, filed on Jul. 8, 2022, which is based on and claims the benefits of priority to Japanese Application No. 2021-134285, filed on Aug. 19, 2021. The entire contents of all of the above applications are incorporated herein by reference.

TECHNICAL FIELD

The present invention relates to a method for producing a polyhydroxyalkanoate and use of the polyhydroxyalkanoate.

BACKGROUND ART

Polyhydroxyalkanoates (may be hereinafter referred to as "PHAs") are known to have biodegradability.

PHAs, which are produced by microorganisms, are accumulated within microbial cells of the microorganisms. As such, in order to use PHA as a plastic, it is necessary to carry out a step of separating PHA from microbial cells of a microorganism and purifying the PHA. The step of separating and purifying PHA involves solubilizing an organism-derived component other than PHA, and then collecting the PHA from an aqueous suspension thus obtained. At this time, for example, a separating operation such as centrifugal separation, filtering, and drying is carried out. However, when a PHA-producing microorganism is inactivated after being cultured, nucleic acids are released from the microbial cells, so that the viscosity of the culture solution is increased. This not only makes it difficult to collect PHA by centrifugation or membrane separation but also makes it difficult to carry out a purification treatment such as an enzyme reaction or an alkaline treatment. For such problems, for example, viscosity reduction treatments such as a heat treatment, addition of hypochlorite, and addition of a commercially available nuclease are known.

Further, Patent Literature 1 discloses a method of adding a peroxide such as hydrogen peroxide to degrade nucleic acids. Patent Literature 2 discloses a technique of adjusting the pH by addition of hydrogen peroxide to improve the efficiency of purification without reducing the molecular weight of 3-hydroxyalkanoate.

CITATION LIST

Patent Literature

Patent Literature 1

Japanese Translation of PCT International Application, Tokuhyohei, No. 08-502415

Patent Literature 2

International Publication No. WO 2004/029266

SUMMARY OF INVENTION

Technical Problem

The above-described conventional techniques, however, have problems such as being unsuitable for industrial-scale use due to increased costs and other factors, and have room for further improvement.

Therefore, it is an object of an aspect of the present invention to provide an industrially easily applicable technology for reducing the viscosity of a culture solution, in order to collect PHA from a PHA-producing microorganism.

Solution to Problem

The inventors of the present invention carried out diligent research in order to attain the object, and newly discovered that, by adding an oxidizer to a culture solution containing a PHA-producing microorganism which has been inactivated, adjusting the pH to a specific pH, and maintaining a specific temperature, it is possible to prevent or reduce an increase in viscosity of the culture solution. Thus, the inventors of the present invention completed the present invention.

Thus, a method for producing a polyhydroxyalkanoate in accordance with an aspect of the present invention (hereinafter referred to as "the present production method") is a method for producing a polyhydroxyalkanoate, including the steps of: (a) maintaining a culture solution at 40° C. to 80° C., the culture solution including microbial cells containing the polyhydroxyalkanoate; and (b) adding an oxidizer to the culture solution obtained in the step (a), adjusting a pH of the culture solution to 10.5 to 13.0, and maintaining the culture solution at 30° C. to 75° C.

An aqueous suspension of a polyhydroxyalkanoate in accordance with an embodiment of the present invention (hereinafter referred to as "the present aqueous suspension") is an aqueous suspension of a polyhydroxyalkanoate, containing hydrogen peroxide and the polyhydroxyalkanoate and having a shear viscosity of 1 mPa·s to 10 mPa·s at 50° C. and 100 1/s.

Advantageous Effects of Invention

According to an aspect of the present invention, it is possible to provide an industrially easily applicable technology for reducing the viscosity of a culture solution, in order to collect PHA from a PHA-producing microorganism.

DESCRIPTION OF EMBODIMENTS

The following description will discuss an embodiment of the present invention in detail. Note that any numerical range expressed as "A to B" in the present specification means "not less than A and not more than B", unless otherwise stated.

1. Overview of Present Invention

As described above, the conventional techniques for reducing an increase in viscosity of a culture solution containing a PHA-producing microorganism which has been inactivated have problems such as not being suitable for industrial-scale use due to increased costs and other factors.

As such, the inventors of the present invention conducted diligent study with an aim to provide, in order to collect PHA from a PHA-producing microorganism, a technology for reducing an increase in viscosity of a culture solution containing a PHA-producing microorganism which has been inactivated. As a result, the inventors of the present invention obtained a new finding that, by adding an oxidizer to a culture solution containing a PHA-producing microorganism which has been inactivated, adjusting the pH of the culture solution to a specific pH, and maintaining a specific temperature of the culture solution, it is possible to prevent or reduce an increase in viscosity of the culture solution. The inventors of the present invention also found that the above method makes it possible to control (promote) a reduction in molecular weight of PHA and to obtain PHA having a desired weight average molecular weight.

According to the present production method, the reduction in viscosity of the culture solution makes it possible to handle the culture solution better. Thus, the culture solution can be used on an industrial scale. Further, in accordance with the reduction in viscosity of the culture solution, the amounts of an enzyme and a surfactant (for example, sodium dodecyl sulfate) required for purification can also be reduced. Thus, the present production method is extremely advantageous in terms of cost.

Furthermore, the configuration described above makes it possible to reduce the amount of plastic waste. This enables the present invention to contribute to achievement of sustainable development goals (SDGs) such as Goal 12 "Ensure sustainable consumption and production patterns" and Goal 14 "Conserve and sustainably use the oceans, seas and marine resources for sustainable development". The following description will discuss the configurations of the present production method and the present aqueous suspension.

2. Method for Producing Polyhydroxyalkanoate

The present production method includes the following steps (a) and (b).

Step (a): maintaining a culture solution at 40° C. to 80° C., the culture solution including microbial cells containing a polyhydroxyalkanoate.

Step (b): adding an oxidizer to the culture solution obtained in the step (a), adjusting a pH of the culture solution to 10.5 to 13.0, and maintaining the culture solution at 30° C. to 75° C.

(Step (a))

The step (a) in the present production method is a step of maintaining a culture solution at 40° C. to 80° C., the culture solution including microbial cells containing a polyhydroxyalkanoate. The step (a) allows inactivating a PHA-producing microorganism. Further, through the step (a), the microbial cells in the culture solution are inactivated at an inactivation temperature in advance. This makes it possible to easily carry out a purification step (described later) and the like.

<Inactivation Temperature>

In the present specification, "inactivation temperature" means a temperature at which it is possible to kill a microorganism in a culture solution. In other words, "inactivation temperature" means a temperature at which it is possible to deactivate catalase, which is an enzyme contained in the microorganism. In an embodiment of the present invention, the inactivation temperature is 40° C. to 80° C., which is a temperature at which the microorganism is killed and catalase is inactivated. The inactivation temperature is preferably 50° C. to 80° C. and more preferably 60° C. to 80° C.

<PHA>

As used herein, the term "PHA" is a generic term for polymers each of which contains a hydroxyalkanoic acid as a monomer unit. A hydroxyalkanoic acid contained in PHA is not limited to any particular one, and can be, for example, 3-hydroxybutanoic acid, 4-hydroxybutanoic acid, 3-hydroxypropionic acid, 3-hydroxypentanoic acid, 3-hydroxyhexanoic acid, 3-hydroxyheptanoic acid, 3-hydroxyoctanoic acid, or the like. The polymers can be a homopolymer, or can be a copolymer containing two or more types of monomer unit.

More specifically, examples of PHA include poly(3-hydroxybutyrate) (P3HB), poly(3-hydroxybutyrate-co-3-hydroxyhexanoate) (P3HB3HH), poly(3-hydroxybutyrate-co-3-hydroxyvalerate) (P3HB3HV), poly(3-hydroxybutyrate-co-4-hydroxybutyrate) (P3HB4HB), poly(3-hydroxybutyrate-co-3-hydroxyoctanoate) (P3HB3HO), poly(3-hydroxybutyrate-co-3-hydroxyoctadecanoate) (P3HB3HOD), poly(3-hydroxybutyrate-co-3-hydroxydecanoate) (P3HB3HD), and poly(3-hydroxybutyrate-co-3-hydroxyvalerate-co-3-hydroxyhexanoate) (P3HB3HV3HH). Among these examples, P3HB, P3HB3HH, P3HB3HV, and P3HB4HB are preferable for being easily produced on an industrial scale.

Further, P3HB3HH, which is a copolymer of 3-hydroxybutyric acid and 3-hydroxyhexanoic acid, is more preferable from the following viewpoints: (i) by changing a composition ratio of repeating units, it is possible to cause a change in melting point and crystallinity and consequently in physical properties, such as Young's modulus and heat resistance, of P3HB3HH and to enable P3HB3HH to have physical properties between the physical properties of polypropylene and the physical properties of polyethylene; and (ii) P3HB3HH is a plastic that is easily produced on an industrial scale as described above and has useful physical properties.

In an embodiment of the present invention, a composition ratio of repeating units in P3HB3HH is such that a composition ratio of a 3-hydroxybutyrate unit to a 3-hydroxyhexanoate unit is preferably 80/20 (mol/mol) to 99.9/0.1 (mol/mol) and more preferably 85/15 (mol/mol) to 97/3 (mol/mol) from the viewpoint of a balance between plasticity and strength. In a case where the composition ratio of the 3-hydroxybutyrate unit to the 3-hydroxyhexanoate unit is not more than 99.9/0.01 (mol/mol), a sufficient plasticity is obtained, and in a case where the composition ratio is not less than 80/20 (mol/mol), a sufficient hardness is obtained.

In an embodiment of the present invention, a weight average molecular weight (may hereinafter be referred to as "Mw") of the PHA obtained in the step (a) is preferably 1,500,000 to 2,500,000, more preferably 1,600,000 to 2,400,000, and even more preferably 1,700,000 to 2,300,000. In a case where the weight average molecular weight of the PHA is within the above range, excellent culture productivity is achieved. The weight average molecular weight of the PHA can be determined as a molecular weight in terms of polystyrene as measured by gel permeation chromatography (GPC) ("Shodex GPC-101" manufactured by Showa Denko K.K.) in which a polystyrene gel ("Shodex K-804" manufactured by Showa Denko K.K.) is used in a column and chloroform is used as a mobile phase.

In an embodiment of the present invention, a solid content concentration of the culture solution obtained in the step (a) is preferably 20% by weight to 40% by weight, more preferably 25% by weight to 40% by weight, and even more preferably 30% by weight to 40% by weight. In a case where the solid content concentration of the culture solution obtained in the step (a) is within the above range, a sufficient amount of PHA can be obtained.

<Microbial Cells>

The microbial cells used in the step (a) are not particularly limited, provided that the microbial cells are of a microorganism capable of producing PHA within a cell of the microorganism. For example, it is possible to use a microorganism isolated from nature, a microorganism deposited at a depositary institution (for example, IFO, ATCC, or the like) for strains, or a mutant, a transformant, or the like that can be prepared from any of those microorganisms. For example, the first P3HB-producing microbial cells (P3HB is an example of PHA) discovered was *Bacillus megaterium* (discovered in 1925), and other examples of P3HB-producing microbial cells include natural microorganisms such as *Cupriavidus necator* (previously classified as *Alcaligenes eutrophus*), *Ralstonia eutropha*, and *Alcaligenes latus*. These microorganisms are known to accumulate PHA within microbial cells of the microorganisms.

Examples of microbial cells that produce a copolymer of hydroxybutyrate and another hydroxyalkanoate (hydroxybutyrate and hydroxyalkanoate are examples of PHA) include *Aeromonas caviae*, which is a microorganism capable of producing P3HB3HV and P3HB3HH, and *Alcaligenes eutrophus*, which is a microorganism capable of producing P3HB4HB. Particularly with respect to P3HB3HH, for example, *Alcaligenes eutrophus* AC32, FERM BP-6038 (T. Fukui, Y. Doi, J. Bateriol., 179, p. 4821-4830 (1997)) into which genes of PHA synthetases have been introduced in order to increase P3HB3HH productivity is more preferable. Besides the above, in accordance with PHA that is desired to be produced, the microbial cells can be of a genetically modified microorganism into which various PHA synthesis-related genes have been introduced.

PHA can also be produced by, for example, a method disclosed in International Publication No. WO 2010/013483. Examples of commercially available PHA include "KANEKA Biodegradable Polymer PHBH (Registered trademark)" (for example, X131A and 151C used in Examples) by KANEKA CORPORATION.

In the present specification, the above-described microorganism capable of producing PHA within cells may be referred to as a "PHA-producing microorganism".

(Step (b))

The step (b) in the present production method is a step of adding an oxidizer to the culture solution obtained in the step (a), adjusting a pH of the culture solution to 10.5 to 13.0, and maintaining the culture solution at 30° C. to 75° C. Note that in the present specification, "viscosity" means a "shear viscosity at 50 and 100 1/s" measured by a method described in the Examples. Further, PHA-containing aqueous suspensions obtained in the step (b) and steps subsequent to the step (b) may each be abbreviated to "aqueous PHA suspension".

The step (b) enables a reduction in viscosity of the resultant culture solution. Reducing the viscosity of the culture solution eliminates the need for dilution with industrial water or the like. Therefore, it is possible to reduce the amount of an enzyme used in a step (c) (described later), so that the cost of producing PHA is reduced. Further, adjusting the weight average molecular weight of PHA makes it possible to produce PHA having a desired weight average molecular weight.

The oxidizer is not limited to any particular one, but examples thereof include hydrogen peroxide ($H_2O_2$), ozone; other inorganic peroxides such as sodium peroxide ($Na_2O_2$), sodium perborate ($Na_2H_4B_2O_8$), sodium percarbonate ($Na_2H_3CO_6$), and sodium persulfate ($Na_2S_2O_8$); similar halogen compounds such as chlorite, chlorate, meta-chloroperbenzoic acid ($C_7HClO_3$) perchlorate, perchloric acid ($ClO_4$), and chlorine dioxide ($ClO_2$); peracids such as performic acid ($CH_2O_3$) and peracetic acid ($CH_3CO_3H$); permanganic acid compounds such as potassium permanganate; sodium perborate; potassium nitrate ($KNO_3$); sodium bismuthate; and cerium (IV) compounds such as ceric ammonium nitrate and cerium sulfate.

Among the above examples, the oxidizer is preferably hydrogen peroxide or ozone for being easily available.

In the step (b), a concentration of hydrogen peroxide in the culture solution is, for example, 0.2% by weight to 30% by weight, preferably 0.2% by weight to 15% by weight, and more preferably 0.2% by weight to 10% by weight. In a case where the concentration of hydrogen peroxide in the culture solution is not less than 0.2% by weight, it is possible to reduce the viscosity of the aqueous PHA suspension. In a case where the concentration of hydrogen peroxide in the culture solution is not more than 30% by weight, it is possible to reduce costs for producing PHA. In the step (b), hydrogen peroxide can be added so as to achieve the above concentration.

In the step (b), an amount of ozone added is, for example, 0.01 g to 0.1 g, preferably 0.02 g to 0.08 g, and more preferably 0.02 g to 0.07 g, per 1 g of PHA-containing biomass. In a case where the amount of ozone added is not less than 0.01 g, it is possible to reduce the viscosity of the aqueous PHA suspension. In a case where the amount of ozone added is not more than 0.1 g, an amount of residual ozone will be small.

In an embodiment of the present invention, in a case where hydrogen peroxide is added, $NaHCO_3$ may be added along with the addition of the hydrogen peroxide. It is expected that $NaHCO_3$ helps the function of the hydrogen peroxide.

In a case where hydrogen peroxide is added in an embodiment of the present invention, a chelating agent may be added along with the addition of the hydrogen peroxide. The addition of the chelating agent enables the hydrogen peroxide solution to be stabilized. The chelating agent is not particularly limited, but examples thereof include sodium silicate, EDTA, and trans-1,2-cyclohexanediamine tetraacetic acid monohydrate.

In the step (b), in order to control a viscosity of the obtained aqueous PHA suspension and a weight average molecular weight of PHA, pH is preferably 10.5 to 13.0, more preferably 10.6 to 12.9, and even more preferably 10.7 to 12.8. In a case where the pH is not less than 10.5, the aqueous PHA suspension has a reduced viscosity and an improved handleability. In a case where the pH is not more than 13.0, there will be sufficient time for adjusting the weight average molecular weight of PHA. The adjustment of pH can be carried out, for example, by addition of an aqueous alkaline solution.

In an embodiment of the present invention, the aqueous alkaline solution is an aqueous solution that contains a basic compound. The basic compound contained in the aqueous alkaline solution is not particularly limited, and examples thereof include: hydroxides of alkali metals or alkaline earth metals such as sodium hydroxide and potassium hydroxide; metal carbonates such as sodium carbonate and potassium carbonate; and metal phosphates or metal hydrogen phosphates such as sodium phosphate, potassium phosphate, sodium hydrogen phosphate, and potassium hydrogen phosphate.

In an embodiment of the present invention, the basic compound contained in the aqueous alkaline solution is preferably an alkali metal hydroxide or an alkaline earth metal hydroxide, and more preferably sodium hydroxide. One of these basic compounds may be used alone, or two or more of these basic compounds may be used in combination.

In the step (b), the order in which addition of an oxidizer and adjustment of the pH are carried out is not particularly limited, but it is preferable that the pH be adjusted after the oxidizer has been added, from the viewpoint of efficiently reducing the pH.

In the step (b), in order to control a viscosity of the aqueous PHA suspension and a weight average molecular weight of PHA, a temperature of the culture solution is preferably 30° C. to 75° C., more preferably 35° C. to 70° C., and even more preferably 40° C. to 65° C. In a case where the temperature of the culture solution is not lower than 30° C., the length of time for adjusting the weight average molecular weight of PHA will not be unnecessarily long. In a case where the temperature of the culture solution is not higher than 80° C., there will be sufficient time for the adjustment.

It is preferable that the aqueous PHA suspension obtained in the step (b) be a Newtonian fluid. In a case where the aqueous PHA suspension is a Newtonian fluid, the dependency of the viscosity on shear rate is low, so that the aqueous PHA suspension is more likely to be homogenous in a stirring device, and the handleability is improved.

In an embodiment of the present invention, the step (b) includes a step of maintaining the adjusted pH preferably for 0.1 hours to 30 hours, more preferably for 0.25 hours to 24 hours, and even more preferably for 0.5 hours to 15 hours. In the step (b), with the degradation of PHA in the culture solution, the pH of the culture solution gradually decreases. As such, by maintaining the pH of the culture solution in the step (b), it is possible to further reduce the viscosity of an obtained aqueous PHA suspension.

In the above-described step of maintaining the pH, a method of maintaining the adjusted pH is not particularly limited, and can be, for example, addition of an aqueous alkaline solution. The aqueous alkaline solution is not particularly limited, and, for example, the above-described aqueous alkaline solution is used.

In an embodiment of the present invention, a temperature in the above-described step of maintaining the pH is not particularly limited, and is, for example, 30° C. to 80° C., and preferably 30° C. to 75° C.

In an embodiment of the present invention, the step (b) may include a step of maintaining the pH at a predetermined temperature for a predetermined amount of time and then at 30° C. to 75° C. for 0.5 hours to 30 hours. As described above, the pH of the culture solution gradually decreases due to degradation of PHA. Thus, by including the step of maintaining the pH of the culture solution at 30° C. to 75° C. for 0.5 hours to 30 hours, it is possible to simplify a neutralization step later.

In an embodiment of the present invention, a weight average molecular weight of PHA in the aqueous PHA suspension obtained in the step (b) is preferably 100,000 to 800,000, more preferably 200,000 to 800,000, and even more preferably 400,000 to 800,000. In a case where the weight average molecular weight is not less than 100,000, sufficient mechanical properties and the like are obtained. In a case where the weight average molecular weight is not more than 800,000, sufficient crystallization speed is obtained and good molding processability is achieved.

In an embodiment of the present invention, a solid content concentration of the aqueous suspension obtained in the step (b) is preferably 20% by weight to 40% by weight, more preferably 25% by weight to 40% by weight, and even more preferably 30% by weight to 40% by weight. In a case where the solid content concentration of the aqueous suspension obtained in the step (b) is within the above range, a sufficient amount of PHA can be obtained.

In an embodiment of the present invention, the present production method may further include steps (c) to (d) below.

Step (c): adding an enzyme to the aqueous suspension obtained in the step (b) to subject the microbial cells to an enzyme treatment.

Step (d): adding a surfactant and an aqueous alkaline solution to the aqueous suspension obtained in the step (c) to adjust the pH of the aqueous suspension to 10.0 to 12.0.

(Step (c))

The step (c) in the present production method is a step of adding an enzyme to the aqueous suspension obtained in the step (b) to subject the microbial cells to an enzyme treatment. Through the step (impurities (for example, cell walls and protein) derived from the microbial cells are disrupted and removed. This allows PHA to be efficiently collected from the microbial cells.

In an embodiment of the present invention, the enzyme treatment in the step (c) can be a lytic enzyme treatment and/or an alkaline proteolytic enzyme treatment. The lytic enzyme treatment and the alkaline proteolytic enzyme treatment are preferably carried out at least once each, and if necessary, the lytic enzyme treatment and/or the alkaline proteolytic enzyme treatment may be carried out twice or more.

In an embodiment of the present invention, the order in which the lytic enzyme treatment and/or the alkaline proteolytic enzyme treatment are/is carried out is not particularly limited.

In carrying out the enzyme treatment (for example, a lytic enzyme treatment and an alkaline proteolytic enzyme treatment) in the step (c), it is preferable that the pH and temperature of the culture solution be adjusted in accordance with the optimum pH and optimum temperature of an enzyme to be used. Methods for adjusting the pH and temperature of the culture solution are not particularly limited, and known methods can be used.

The step (c) may include a step of adding a surfactant. The addition of the surfactant in the step (c) can be carried out before, simultaneously with, or after addition of an alkaline proteolytic enzyme. The addition of the surfactant in the step (c) is preferably carried out after the addition of the alkaline proteolytic enzyme. The addition of the surfactant in the step (c) enables impurities (for example, nucleic acids and protein) derived from the microbial cells to be dispersed and lysed, so that PHA with high purity can be separated from the microbial cells.

<Lytic Enzyme Treatment>

In an embodiment of the present invention, the lytic enzyme treatment is a step of adding a lytic enzyme to the culture solution to subject the microbial cells to an enzyme treatment.

As used herein, the term “lytic enzyme” means an enzyme that has the activity of degrading (subjecting to lysis) cell walls (for example, peptidoglycan) of microbial cells.

In an embodiment of the present invention, the lytic enzyme is not particularly limited, and examples thereof include lysozyme, labyrinthine, β-N-acetylglucosaminidase, endolysin, and autolysin. Lysozyme is preferable from the viewpoint of being economically advantageous. One of these lytic enzymes may be used alone, or two or more of these lytic enzymes may be used in combination.

As the lytic enzyme, a commercially available lytic enzyme can also be used. Examples of the commercially available lytic enzyme include "Lysozyme" and "Achromopeptidase" manufactured by FUJIFILM Wako Pure Chemical Corporation.

In an embodiment of the present invention, the optimum pH of the lytic enzyme is not particularly limited, provided that the lytic enzyme has cell wall degradation activity. The optimum pH of the lytic enzyme is, for example, 5.0 to 11.0, preferably 6.0 to 9.0, and more preferably 6.0 to 8.0.

In an embodiment of the present invention, the optimum temperature of the lytic enzyme is not particularly limited, but is preferably not higher than 60° C., and more preferably not higher than 50° C., from the viewpoint of eliminating the need for excessive heating and preventing thermal change (thermal decomposition) of PHA. A lower limit of the optimum temperature is not particularly limited, but is preferably a temperature that is not lower than room temperature (for example, 25° C.), from the viewpoint of eliminating the need for excessive cooling operation and being economical.

<Alkaline Proteolytic Enzyme Treatment>

As used herein, the term "alkaline proteolytic enzyme" means a proteolytic enzyme having the activity of degrading protein in an alkaline environment (for example, in a solution that is pH 8.5).

In addition, as used herein, the term "alkaline proteolytic enzyme treatment" means a step of adding the alkaline proteolytic enzyme to the culture solution to subject the microbial cells to an enzyme treatment.

In an embodiment of the present invention, the alkaline proteolytic enzyme is not particularly limited, provided that the alkaline proteolytic enzyme has the activity of degrading protein in an alkaline environment. Examples of the alkaline proteolytic enzyme include serine-specific proteolytic enzymes (for example, subtilisin, chymotrypsin, and trypsin), cysteine-specific proteolytic enzymes (for example, papain, bromelain, and cathepsin), and aspartic acid-specific proteolytic enzymes (for example, pepsin, cathepsin D, and HIV protease). From the viewpoint of being economically advantageous, serine-specific proteolytic enzymes, and subtilisin (for example, alcalase), in particular, are preferable. One of these alkaline proteolytic enzymes may be used alone, or two or more of these alkaline proteolytic enzymes may be used in combination.

As the alkaline proteolytic enzyme, a commercially available alkaline proteolytic enzyme can be used. Examples of the commercially available alkaline proteolytic enzyme include: "Alcalase 2.5 L" manufactured by Novozyme; "Protin SD-AY10" and "Protease P (Amano) 3SD" manufactured by Amano Enzyme Inc.; "Multifect PR6L" and "Optimase PR89L" manufactured by Danisco Japan Ltd.; "Sumizyme MP" manufactured by Shin Nihon Chemical Co., Ltd.; "Delvolase" manufactured by DSM Japan K.K.; "Biopurase OP", "Biopurase SP-20FG", and "Biopurase SP-4FG" manufactured by Nagase ChemteX Corporation; "Orientase 22BF" manufactured by HBI Enzymes Inc.; and "AROASE XA-10" manufactured by Yakult Pharmaceutical Industry Co., Ltd.

In an embodiment of the present invention, the optimum pH of the alkaline proteolytic enzyme is not particularly limited, provided that the alkaline proteolytic enzyme has activity in an alkaline environment. The optimum pH of the alkaline proteolytic enzyme is, for example, 8.0 to 14.0, preferably 8.0 to 12.0, more preferably 8.0 to 10.0, even more preferably 8.0 to 9.0, and most preferably 8.5.

In an embodiment of the present invention, the optimum temperature of the alkaline proteolytic enzyme is not particularly limited, but is preferably not higher than 60° C., and more preferably not higher than 50° C., from the viewpoint of eliminating the need for excessive heating and preventing thermal change (thermal decomposition) of P3HA. A lower limit of the optimum temperature is not particularly limited, but is preferably a temperature that is not lower than room temperature (for example, 25° C.), from the viewpoint of eliminating the need for excessive cooling operation and being economical.

In an embodiment of the present invention, the enzyme treatment in the step (c) can be carried out with a combination of lysozyme and alcalase.

(Step (d))

The step (d) in the present production method is a step of adding a surfactant and an aqueous alkaline solution to the aqueous suspension obtained in the step (c) to adjust the pH of the aqueous suspension to 10.0 to 12.0. The step (d) preferably includes step (d1) and step (d2) below.

Step (d1): adding an aqueous alkaline solution to the culture solution obtained in the step (c) to adjust the pH of the culture solution to 10.0 to 12.0.

Step (d2): adding a surfactant.

<Step (d1)>

The step (d1) is, as described above, a step of adding an aqueous alkaline solution to the aqueous PHA suspension obtained in the step (c) to adjust the pH of the aqueous PHA suspension to 10.0 to 12.0. Through the step (d1), impurities (for example, nucleic acids and protein) derived from the microbial cells are dispersed and lysed. This allows PHA with high purity to be separated from the microbial cells.

For the aqueous alkaline solution in the step (d1), the description under the (Step (b)) section is incorporated by reference.

In the step (d1), the aqueous alkaline solution is added to adjust the pH to preferably 10.0 to 12.0, more preferably 10.2 to 11.8, and even more preferably 10.4 to 11.6. Adjusting the pH to not less than 10.0 provides the advantage of making it possible to disrupt and lyse the microbial cell component. In addition, adjusting the pH to not more than 12.0 makes it possible to prevent unintended damage to the microbial cells.

The temperature in the step (d1) is preferably lower than 100° C., and more preferably lower than 80° C. A lower limit of the temperature in the step (d1) is not particularly limited, and is, for example, preferably not lower than 40° C.

<Step (d2)>

The step (d2) is a step of adding a surfactant to the culture solution. The step (d2) enables efficient treatment of impurities contained in the microbial cells, cell membranes in particular, and enables removal of more impurities derived from the microbial cells, so that PHA with higher purity can be separated from the microbial cells.

In an embodiment of the present invention, the surfactant is not particularly limited, but examples of the surfactant include anionic surfactants, cationic surfactants, amphoteric surfactants, and nonionic surfactants. Among these surfactants, anionic surfactants are preferable from the viewpoint of having high ability to remove cell membranes. One of these surfactants may be used alone, or two or more of these surfactants may be used in combination.

Examples of the anionic surfactants include alkyl sulfates, alkylbenzene sulfonates, alkyl sulfate ester salts, alkenyl sulfate ester salts, alkyl ether sulfate ester salts, alkenyl ether sulfate ester salts, α-olefin sulfonates, α-sulfofatty acid salts, esters of α-sulfofatty acid salts, alkyl ether carboxylates, alkenyl ether carboxylates, amino acid-type surfactants, and N-acylamino acid type surfactants. Among these anionic surfactants, alkyl sulfate ester salts are preferable, and sodium dodecyl sulfate (SDS) is particularly preferable from the viewpoint of having high ability to remove cell membranes and being inexpensive. One of these anionic surfactants may be used alone, or two or more of these anionic surfactants may be used in combination.

In the step (d), the amount of surfactant to be added is not particularly limited, and is, for example, 0.1% by weight to 5.0% by weight, and preferably 0.3% by weight to 2.5% by weight, relative to the culture solution.

The step (d2) can be carried out before, simultaneously, or after the step (d1). That is, the addition of the surfactant and the aqueous alkaline solution in the step (d) can be carried out in any of the following manners: the aqueous alkaline solution is added to adjust the pH, and then the surfactant is added; the surfactant and the aqueous alkaline solution are simultaneously added to adjust the pH; and the surfactant is added, and then the aqueous alkaline solution is added to adjust the pH.

<Step (e)>

In an embodiment of the present invention, the present production method can further include a step (e).

The step (e) is a step of centrifuging the aqueous PHA suspension obtained in the step (d) and removing a supernatant to obtain an aqueous PHA suspension in which PHA is concentrated. That is, the step (e) is a step of removing impurities from PHA separated from the microbial cells and concentrating and purifying the PHA.

In the step (d), a method for centrifuging the culture solution is not particularly limited, and a known method can be used.

In the step (e), after the centrifugation of the culture solution and the removal of the supernatant, it is preferable to repeatedly carry out an operation in which a solution is added to a precipitate, another centrifugation is carried out, and a supernatant is removed. With this operation, it is possible to obtain a more concentrated and purified aqueous PHA suspension. Here, the solution added after the removal of the supernatant is preferably an aqueous alkaline solution that has been adjusted to the same pH as that of the culture solution. In an embodiment of the present invention, the solution is preferably the same as the aqueous alkaline solution used in the step (d).

The amount of the impurities which are to remain in an end product is substantially determined by the step (d), and it is preferable to minimize the impurities. Of course, depending on the purpose of use, it may be acceptable to have the impurities mixed in the end product, provided that the physical properties of the end product are not impaired. However, in a case where a highly pure PHA is required, for example, for medical use, it is preferable to minimize the impurities. In so doing, an index of purification degree can be, for example, an amount of protein remaining in the aqueous PHA suspension (residual protein content). The amount of protein in the aqueous PHA suspension is not particularly limited, provided that the residual protein content of the PHA powder can be achieved. The amount of protein is preferably not more than 3,000 ppm, more preferably not more than 2,500 ppm, and even more preferably not more than 2,000 ppm per weight of PHA in the aqueous PHA suspension.

A solvent (the "solvent" may also be referred to as "aqueous medium") contained in the aqueous PHA suspension in the step (e) is not particularly limited and can be selected from water and a mixed solvent of water and an organic solvent. In the mixed solvent, the concentration of the organic solvent is not particularly limited, provided that the concentration is equal to or lower than the solubility, in water, of the organic solvent used. The organic solvent is not particularly limited. Examples of the organic solvent include: alcohols such as methanol, ethanol, 1-propanol, 2-propanol, 1-butanol, 2-butanol, iso-butanol, pentanol, hexanol, and heptanol; ketones such as acetone and methyl ethyl ketone; ethers such as tetrahydrofuran and dioxane; nitriles such as acetonitrile and propionitrile; amides such as dimethylformamide and acetamide; dimethyl sulfoxide, pyridine, and piperidine. Among these examples, methanol, ethanol, 1-propanol, 2-propanol, 1-butanol, 2-butanol, iso-butanol, acetone, methyl ethyl ketone, tetrahydrofuran, dioxane, acetonitrile, propionitrile, and the like are preferable for being easy to remove. Further, methanol, ethanol, 1-propanol, 2-propanol, butanol, acetone, and the like are more preferable for being easily available. Furthermore, methanol, ethanol, and acetone are particularly preferable.

The amount of water contained in the aqueous medium which is contained in the aqueous PHA suspension is preferably not less than 5% by weight, more preferably not less than 10% by weight, even more preferably not less than 30% by weight, and particularly preferably not less than 50% by weight.

Note that the aqueous PHA suspension in the step (e) may contain another solvent, a microbial cell-derived component, a compound which is generated during purification, and/or the like, provided that the essentials of the present invention are not impaired.

3. Aqueous Suspension of Polyhydroxyalkanoate

The present aqueous PHA suspension is an aqueous suspension of PHA containing hydrogen peroxide and polyhydroxyalkanoate and having a shear viscosity of 1 mPa·s to 10 mPa·s at 50° C. and 100 l/s. Due to being low in viscosity, the present aqueous PHA suspension is excellent in handleability and makes it possible to efficiently produce PHA.

A shear viscosity of the present aqueous PHA suspension at 50° C. and 100 l/s is 1 mPa·s to 10 mPa·s, preferably 1 mPa·s to 9 mPa·s, and more preferably 1 mPa·s to 8 mPa·s. A shear viscosity of the present aqueous PHA suspension at 50° C. and 10 l/s is, for example, 1 mPa·s to 20 mPa·s, preferably 1 mPa·s to 18 mPa·s, and more preferably 1 mPa·s to 15 mPa·s. In a case where the present aqueous PHA suspension has a shear viscosity within the above range, the present aqueous PHA suspension has the advantage of being excellent in handleability. A shear viscosity of the present aqueous PHA suspension is measured by a method described in the Examples.

In an embodiment of the present invention, a solid content concentration of the present aqueous PHA suspension is, for example, 20% by weight to 40% by weight, and preferably 25% by weight to 40% by weight. Ordinarily, an aqueous suspension having a solid content concentration of 20% by weight to 40% by weight has a high viscosity which makes it difficult to carry out the subsequent purification treatment. However, the present aqueous PHA suspension, though having such a high solid content concentration, can provide an aqueous suspension with a reduced increase in viscosity, because the present aqueous PHA suspension contains hydrogen peroxide. A solid content concentration of the present aqueous PHA suspension is measured by a method described in the Examples.

A weight average molecular weight of PHA contained in the present aqueous PHA suspension is, for example, 100, 000 to 800,000, preferably 100,000 to 800,000, more preferably 200,000 to 800,000, and even more preferably 400,000 to 800,000. In a case where the weight average molecular weight is not less than 100,000, sufficient mechanical properties and the like are obtained. In a case where the weight average molecular weight is not more than 800,000, sufficient crystallization speed is obtained and good molding processability is achieved.

A concentration of hydrogen peroxide in the present aqueous PHA suspension is, for example, 0.2% by weight to 30% by weight, preferably 0.2% by weight to 15% by weight, and more preferably 0.2% by weight to 10% by weight. In a case where the concentration of hydrogen peroxide in the present aqueous PHA suspension is not less than 0.2% by weight, it is possible to reduce the viscosity of the aqueous PHA suspension. In a case where the concentration of hydrogen peroxide in the present aqueous PHA suspension is not more than 30% by weight, it is possible to reduce costs for producing PHA.

The present aqueous PHA suspension can contain various components produced or not removed during the present production method, provided that an effect of the present invention is exhibited.

The present invention is not limited to the embodiments, but can be altered by a skilled person in the art within the scope of the claims. The present invention also encompasses, in its technical scope, any embodiment derived by combining technical means disclosed in differing embodiments.

That is, an aspect of the present invention encompasses the following.

<1> A method for producing a polyhydroxyalkanoate, including the steps of:

(a) maintaining a culture solution at 40° C. to 80° C., the culture solution including microbial cells containing a polyhydroxyalkanoate; and (b) adding an oxidizer to the culture solution obtained in the step (a), adjusting a pH of the culture solution to 10.5 to 13.0, and maintaining the culture solution at 30° C. to 75° C.

<2> The method as set forth in <1>, wherein the oxidizer is a hydrogen peroxide solution or ozone.

<3> The method as set forth in <1> or <2>, further including the steps of:

(c) adding an enzyme to an aqueous suspension obtained in the step (b) to subject the microbial cells to an enzyme treatment; and (d) adding a surfactant and an aqueous alkaline solution to the aqueous suspension obtained in the step (c) to adjust a pH of the aqueous suspension to 10.0 to 12.0.

<4> The method as set forth in any one of <1> to <3>, wherein:

the polyhydroxyalkanoate in the culture solution obtained in the step (a) has a weight average molecular weight of 1,500,000 to 2,500,000; and the culture solution obtained in the step (a) has a solid content concentration of 20% by weight to 40% by weight.

<5>

The method as set forth in any one of <1> to <4>, wherein the step (b) includes a step of maintaining, for 0.1 hours to 30 hours, the pH which has been adjusted.

<6>

The method as set forth in any one of <1> to <5>, wherein:

the polyhydroxyalkanoate in the aqueous suspension obtained in the step (b) has a weight average molecular weight of 100,000 to 800,000; and the aqueous suspension obtained in the step (b) has a solid content concentration of 20% by weight to 40% by weight.

<7> The method as set forth in any one of <1> to <6>, wherein, in the step (b), in a case where hydrogen peroxide is added to the culture solution, the hydrogen peroxide is added such that a concentration of the hydrogen peroxide in the culture solution is 0.2% by weight to 30% by weight.

<8> The method as set forth in any one of <3> to <7>, wherein the enzyme in the step (c) is a lytic enzyme and/or an alkaline proteolytic enzyme.

<9> The method as set forth in any one of <3> to <8>, wherein the step (c) includes a step of adding a surfactant.

<10> An aqueous suspension of a polyhydroxyalkanoate, containing hydrogen peroxide and the polyhydroxyalkanoate and having a shear viscosity of 1 mPa·s to 10 mPa·s at 50° C. and 100 1/s.

<11> The aqueous suspension as set forth in <10>, having a solid content concentration of 20% by weight to 40% by weight.

<12> The aqueous suspension as set forth in <10> or <11>, wherein the polyhydroxyalkanoate has a weight average molecular weight of 100,000 to 800,000.

<13> The aqueous suspension as set forth in any one of <10> to <12>, wherein a concentration of the hydrogen peroxide is 0.2% by weight to 30% by weight.

EXAMPLES

The following description will discuss embodiments of the present invention in further detail on the basis of Examples. However, the present invention is not limited by the Examples. Note that, in the Examples, "PHBH" is used as "PHA", and "PHA" can be read as "PHBH".

[Measurement Method]

In Examples and Comparative Examples, measurement was carried out by the following method.

(Shear Viscosity of Aqueous PHA Suspension)

A viscosity of an aqueous PHA suspension was measured by the following method. Specifically, with MCR302 manufactured by Anton-Paar GmbH, the viscosity was measured in a coaxial double cylinder. 20 mL of the aqueous PHA suspension was introduced into the cylinder and the temperature of the aqueous PHA suspension was adjusted to 50° C. After the intended shear rate was reached, a viscosity was measured when a change in torque over time had become less than 1%.

(Residual Protein Content)

The residual protein content of the PHA powder was measured using BCA Protein Assay Kit (manufactured by Thermo Fisher Scientific Inc.). Specifically, 10 mg of PHBH powder was introduced into 15-mL falcon tube, and 2 mL of a reagent in the above kit was added, followed by shaking at 60° C. for 30 minutes. After 30 minutes from the end of shaking, the temperature was reduced to 25° C., and the absorbance at a wavelength of 562 nm was measured.

(Weight Average Molecular Weight)

A culture solution containing PHA after inactivation was diluted with distilled water and centrifuged, and a supernatant was then removed. Ethanol was added to a resulting precipitate (PHA) so that the precipitate was dispersed in ethanol, and centrifugation was carried out. A supernatant was removed and dried using a vacuum dryer for not less than 1 hour to completely dry a precipitate, so that dry matter (PHA powder) was obtained. After 10 mg of the obtained PHA powder had been dissolved in 10 mL of chloroform, insoluble matter was removed by filtration. The initial molecular weight of this solution (filtrate) was measured using a GPC system manufactured by Shimadzu Corporation equipped with "Shodex K805L (300 mm×8 mm, two columns connected)" (manufactured by Showa Denko K.K.) with chloroform as a mobile phase. Shodex K-804 (polystyrene gel) manufactured by Showa Denko K.K. was used as a molecular weight standard sample.

(Solid Content Concentration)

A solid content concentration the culture solution containing PHA after inactivation was measured with a heat drying type moisture analyzer ML-50 (manufactured by A&D Company, Limited). The culture solution was heated at 130° C. until a rate of weight change was lower than 0.05%/min, and a solid content concentration was determined from a change in weight before and after heating.

(Hydrogen Peroxide Concentration)

The culture solution containing PHA after molecular weight adjustment was centrifuged. Then, 1 ml of the supernatant was separated and subjected to measurement of a hydrogen peroxide concentration with a measurement tube of "PACKTEST Hydrogen Peroxide (High Range)" (manufactured by KYORITSU CHEMICAL-CHECK Lab., Corp.).

Example 1

(Preparation of Microbial Cell Culture Solution)

*Ralstonia eutropha* described in International Publication No. WO 2019/142717 was cultured by a method described in paragraphs [0041] to [0048] of the same document to obtain a microbial cell culture solution including microbial cells containing PHA. Note that *Ralstonia eutropha* is currently classified as *Cupriavidus necator*. A composition ratio (a composition ratio of a 3HB unit to a 3HH unit) of repeating units of PHA was 85/15 (mol/mol) to 92/8 (mol/mol).

(Sep (a)) (Inactivation)

The microbial cell culture solution obtained above was subjected to heating and stirring at an internal temperature of 60° C. to 70° C. for 7 hours for sterilization to obtain an inactivated culture solution. The PHA in the inactivated culture solution had a weight average molecular weight of 1,800,000. The inactivated culture solution had a solid content concentration of 30% by weight.

(Step (b)) (Viscosity Reduction Treatment)

To the inactivated culture solution obtained above, hydrogen peroxide (manufactured by FUJIFILM Wako Pure Chemical Corporation) was added to achieve a concentration indicated in Table 1. Then, a 30% aqueous sodium hydroxide solution was added to adjust the pH to 11.0. While the solution was maintained at 60° C., the addition of the 30% aqueous sodium hydroxide solution was continued to maintain the pH at 11.0 for a time indicated in Table 1. Thus obtained was an aqueous PHA suspension. The results are shown in Table 1. Note that the solid content concentration after the viscosity reduction treatment was 28% by weight to 30% by weight.

Comparative Example 1

An aqueous PHA suspension was obtained in the same manner as in Example 1 except that the pH, the hydrogen peroxide concentration, and the reaction time were changed as indicated in Table 2. The results are shown in Table 2.

TABLE 1

| | pH | Hydrogen peroxide [wt %] | Reaction time [hr] | Viscosity (50° C., 10 1/s) [mPa · s] | Viscosity (50° C., 100 1/s) [mPa · s] |
|---|---|---|---|---|---|
| Example 1-1 | 11 | 0.66 | 0.66 | 4.38 | 4.18 |
| Example 1-2 | 11 | 0.66 | 1 | 5.01 | 4.98 |
| Example 1-3 | 11 | 0.66 | 1.5 | 5.71 | 4.91 |
| Example 1-4 | 11 | 0.66 | 2 | 6.19 | 5.92 |
| Example 1-5 | 11 | 0.66 | 2.34 | 5.44 | 4.59 |
| Example 1-6 | 11 | 1.21 | 1.5 | 7.82 | 4.66 |
| Comparative Example 1-1 | 11 | 0.00 | 0 | 59.33 | 30.19 |
| Comparative Example 1-2 | 10 | 0.00 | 0 | 90.01 | 36.26 |
| Comparative Example 1-3 | 10 | 0.33 | 1 | 239.77 | 76.21 |
| Comparative Example 1-4 | 10 | 0.99 | 1 | 218.84 | 75.22 |
| Comparative Example 1-5 | 10 | 0.33 | 2 | 244.49 | 81.30 |
| Comparative Example 1-6 | 10 | 0.99 | 2 | 164.23 | 64.99 |

As indicated in Table 1, it was found that each of the aqueous PHA suspensions of Examples 1-1 to 1-6 had a significantly low viscosity regardless of the reaction time. Further, since no shear rate dependency was observed, these aqueous PHA suspensions were found to be Newtonian fluids. In a case where the reaction was carried out at a hydrogen peroxide concentration of 0.66% for 1 hour (Example 1-2), the weight average molecular weight of PHA was 740,000. In a case where the reaction was carried out at a hydrogen peroxide concentration of 0.66% for 1.5 hours (Example 1-3), the weight average molecular weight of PHA was 550,000. In a case where the reaction was carried out at a hydrogen peroxide concentration of 0.66% for 2 hours (Example 1-4), the weight average molecular weight of PHA was 430,000. The weight average molecular weights of PHA were reduced compared with those in the culture solutions before the viscosity reduction treatment.

In contrast, the aqueous PHA suspension of Comparative Example 1-1 had a viscosity higher than those of the aqueous PHA suspensions of Examples 1-1 to 1-6. It was thus found that addition of hydrogen peroxide is an important factor for reducing viscosity. Further, in cases where the pH was 10.0, the aqueous PHA suspensions of Comparative Examples 1-2 to 1-6 each had a viscosity higher than those of the aqueous PHA suspensions of Examples 1-1 to 1-6. It was thus found that pH is an important factor for reducing viscosity. The weight average molecular weight of PHA in (Comparative Example 1-1) was 1,800,000, and the weight average molecular weight of PHA in a case where the reaction was carried out at a hydrogen peroxide concentration of 0.99% for 1 hour (Comparative Example 1-4) was 1,600,000.

Example 2

An aqueous PHA suspension was obtained in the same manner as in Example 1 except that the pH, the hydrogen peroxide concentration, and the reaction time were changed as indicated in Table 2. The results are shown in Table 2.

Comparative Example 2

An aqueous PHA suspension was obtained in the same manner as in Example 1 except that the hydrogen peroxide concentration and the reaction time were changed as indicated in Table 2. The results are shown in Table 2.

TABLE 2

| | pH | Hydrogen peroxide [wt %] | Reaction time [hr] | Viscosity (50° C., 10 1/s) [mPa · s] | Viscosity (50° C., 100 1/s) [mPa · s] |
|---|---|---|---|---|---|
| Example 2-1 | 12.0 | 0.33 | 1 | 10.85 | 5.96 |
| Example 2-2 | 12.0 | 0.99 | 1 | 10.35 | 4.58 |
| Example 2-3 | 12.0 | 0.99 | 2 | 9.58 | 4.36 |
| Comparative Example 2-1 | 12.0 | 0.00 | 0 | 42.12 | 21.36 |

As indicated in Table 2, it was found that, in a case where the pH was 12.0, each of the aqueous PHA suspensions of Examples 2-1 to 2-3, to which hydrogen peroxide was added, had a reduced viscosity. Meanwhile, Comparative Example 2-1 had a high viscosity of the aqueous PHA suspension in comparison to Examples 2-1 to 2-3. It was thus found that addition of hydrogen peroxide contributes to reduction of the viscosity of an aqueous PHA suspension, even in a case where the pH of the aqueous PHA suspension is as high as 12.0.

Example 3

An aqueous PHA suspension was obtained in the same manner as in Example 1 except that the pH, the hydrogen peroxide concentration, and the reaction time were changed as indicated in Table 3. The results are shown in Table 3.

TABLE 3

| | pH | Hydrogen peroxide [wt %] | Reaction time [hr] | Viscosity (50° C., 10 1/s) [mPa · s] | Viscosity (50° C., 100 1/s) [mPa · s] |
|---|---|---|---|---|---|
| Example 3-1 | 12.7 | 0.66 | 1.5 | 13.86 | 5.17 |

As indicated in Table 3, it was found that even in a case where the pH of an aqueous PHA suspension was is further increased to 12.7, the viscosity of the aqueous PHA suspension is reduced by addition of hydrogen peroxide.

Example 4

An aqueous PHA suspension was obtained in the same manner as in Example 1 except that the hydrogen peroxide concentration, the reaction temperature, and the reaction time were changed as indicated in Table 4. The results are shown in Table 4.

TABLE 4

| | pH | Hydrogen peroxide [wt %] | Temperature [° C.] | Reaction time [hr] | Viscosity (50° C., 10 1/s) [mPa · s] | Viscosity (50° C., 100 1/s) [mPa · s] | Weight average molecular weight of PHA | Amount of residual hydrogen peroxide [ppm] |
|---|---|---|---|---|---|---|---|---|
| Example 4-1 | 11 | 0.66 | 40 | 24 | 5.83 | 4.48 | 710,000 | 300 to 400 |
| Example 4-2 | 11 | 0.66 | 50 | 7 | 5.53 | 3.9 | 720,000 | 700 to 1,000 |
| Example 4-3 | 11 | 0.66 | 60 | 1 | 5.01 | 4.98 | 740,000 | not less than 1,000 |

As indicated in Table 4, it was found that controlling the temperature and the reaction time makes it possible to achieve a desired viscosity of the aqueous PHA suspension and a desired weight average molecular weight of the PHA.

Example 5

(Step (c)) (Enzyme Treatment)

The aqueous PHA suspensions of Examples 1 to 3 were each adjusted so as to have a pH of 7.0±0.2 by addition of 10% sulfuric acid thereto. A solid content concentration of each aqueous PHA suspension to which the sulfuric acid had been added was measured to be 30% by weight. After the addition of the sulfuric acid, lysozyme (manufactured by FUJIFILM Wako Pure Chemical Corporation), which is a lytic enzyme that degrades sugar chains (peptidoglycan) in the cell walls, was added such that a concentration of lysozyme in the aqueous PHA suspension was 10 ppm, and the aqueous PHA suspension was held at 50° C. for 2 hours. After that, Alcalase 2.5 L (manufactured by Novozyme), which is a proteolytic enzyme, was added so that a concentration of Alcalase 2.5 L in the aqueous PHA suspension was 300 ppm. Subsequently, 30% sodium hydroxide was added at 50° C., and the aqueous PHA suspension was maintained for 2 hours while being adjusted so as to have a pH of 8.5.

(Step (d)) (Alkaline Treatment)

Sodium dodecyl sulfate (SDS, manufactured by Kao Corporation) was added to the above enzyme-treated solution so as to be 0.6 wt % to 1.0 wt %. After that, the enzyme-treated solution was adjusted with use of an aqueous sodium hydroxide solution so as to have a pH of 11.0±0.2. Then, the enzyme-treated solution was centrifuged (4,500 rpm, 10 minutes), and then a supernatant was removed to obtain an aqueous PHA suspension which had been concentrated by 2 folds. The following operation was repeated 3 times: adding, to the concentrated aqueous PHA suspension, sodium hydroxide in an amount equal to that of the removed supernatant; centrifuging the aqueous PHA suspension again (4,500 rpm, 10 minutes); and removing a supernatant. The concentration of residual protein in the obtained aqueous PHA suspension was 1,217 ppm. The results are shown in Table 5.

Example 6

A treatment was carried out in the same manner as in Example 5 except that the concentration of lysozyme was changed to 5 ppm and the concentration of Alcalase 2.5 L was changed to 150 ppm. The concentration of residual protein in the obtained aqueous PHA suspension was 1,645 ppm. The results are shown in Table 5.

Comparative Example 3

A treatment was carried out in the same manner as in Example 1 up to the inactivation treatment, and the solution was held at pH 11.0 for 1.5 hours. The viscosity at 50° C. and a shear rate of 10 l/s was 60.17 mPa·s, and the handleability was poor. In order to improve handleability, industrial water (IW) was added to dilute the solution so as to achieve a solid content concentration of 18%. The subsequent operations were carried out in the same manner as in Example 5. The concentration of residual protein in the obtained aqueous PHA suspension was 1,675 ppm. The results are shown in Table 5.

TABLE 5

| | Solid content concentration [wt %] | Amount of lysozyme added [ppm] | Amount of alcalase added [ppm] | Amount of SDS added [ppm] | Residual protein concentration [ppm] |
|---|---|---|---|---|---|
| Example 5 | 30 | 10 | 300 | 0.67 | 1217 |
| Example 6 | 30 | 5 | 150 | 0.67 | 1645 |
| Comparative Example 3 | 18 | 10 | 300 | 0.67 | 1675 |

As indicated in Table 5, Comparative Example 3 was poor in handleability of the aqueous PHA suspension in comparison to Examples 5 and 6, because hydrogen peroxide treatment was not carried out in Comparative Example 3. As such, it was necessary to dilute the aqueous PHA suspension in order to proceed with a subsequent step. As a result, the volume of the aqueous PHA suspension increased, so that the amounts of an enzyme and SDS required in a subsequent step increased.

Further, in each of Examples 5 and 6, the speed of the reaction by the enzyme was fast in comparison to Comparative Example 3. This is presumed to be due to the low viscosity of the aqueous PHA suspension. These results show that, according to Examples 5 and 6, protein (PHA) can be produced in an amount equivalent to or larger than that in Comparative Example 3, while using reduced amounts of the enzyme and the SDS in comparison to Comparative Example 3.

Example 7

(Step (c)) (Enzyme Treatment)

To each of the aqueous PHA suspensions of Examples 1 to 3, Esperase (manufactured by Novozyme), which is an alkaline proteolytic enzyme, was added such that a concentration of Esperase in the aqueous PHA suspension was 100 ppm. Subsequently, 30% sodium hydroxide was added at 50° C., and a resulting mixture was maintained for 2 hours while being adjusted so as to have a pH of 11.0. Then, the mixture was centrifuged (4,500 rpm, 10 minutes), and then a supernatant was removed to obtain an aqueous PHA suspension which had been concentrated by 2 folds. To the concentrated aqueous PHA suspension, sodium hydroxide was added in an amount equal to that of the removed supernatant to obtain an aqueous PHA suspension. The aqueous PHA suspension was adjusted so as to have a pH of 7.0±0.2 by addition of 10% sulfuric acid thereto. A solid content concentration of the aqueous PHA suspension to which the sulfuric acid had been added was measured to be 30% by weight. After the addition of the sulfuric acid, lysozyme, which is a lytic enzyme that degrades sugar chains in the cell walls, was added such that a concentration of lysozyme in the aqueous PHA suspension was 10 ppm, and the aqueous PHA suspension was held at 50° C. for 2 hours. After that, Alcalase 2.5 L, which is a proteolytic enzyme, was added such that a concentration Alcalase 2.5 L in the aqueous PHA suspension was 300 ppm. Then, 30% sodium hydroxide was added at 50° C., and the aqueous PHA suspension was maintained for 2 hours while being adjusted so as to have a pH of 8.5.

(Step (d)) (Alkaline Treatment)

SDS was added to the enzyme-treated solution so as to be 0.3 wt % to 1.0 wt %. After that, the enzyme-treated solution was adjusted with use of an aqueous sodium hydroxide solution so as to have a pH of 11.0±0.2, and was reacted at 40° C. for 1 hour. Then, the enzyme-treated solution was centrifuged (4,500 rpm, 10 minutes), and then a supernatant was removed to obtain an aqueous PHA suspension which had been concentrated by 2 folds. The following operation was repeated 3 times: adding, to the concentrated aqueous PHA suspension, sodium hydroxide in an amount equal to that of the removed supernatant; centrifuging the aqueous PHA suspension again (4,500 rpm, 10 minutes); and removing a supernatant. A concentration of residual protein in the obtained aqueous PHA suspension was 926 ppm.

Example 8

A treatment was carried out in the same manner as in Example 7 up to the alkaline treatment, except that Esperase was not added. A concentration of residual protein in the obtained aqueous PHA suspension was 1,244 ppm.

TABLE 6

| | Solid content concentration [wt %] | Amount of Esperase added [ppm] | Amount of alcalase added [ppm] | Amount of SDS added [ppm] | Residual protein concentration [ppm] |
|---|---|---|---|---|---|
| Example 7 | 30 | 100 | 300 | 0.67 | 926 |
| Example 8 | 30 | 0 | 300 | 0.67 | 1244 |

As indicated in Table 6, a sufficient amount of protein was obtained in both Examples 7 and 8. Example 8 had a high protein concentration in comparison to Example 7, presumably due to containing impurities. It was thus shown that carrying out a treatment with Esperase makes it possible to obtain PHA with higher purity.

Thus, it was found that the present production method makes it possible to obtain an aqueous PHA suspension having low viscosity and excellent handleability and to obtain PHA having a desired weight average molecular weight. It was also found that the aqueous PHA suspension can reduce the amounts of materials required for purification treatment and is therefore advantageous in terms of cost.

INDUSTRIAL APPLICABILITY

The present production method makes it possible to produce PHA with a simple operation, and thus can be advantageously used in production of PHA.

The invention claimed is:

1. A method for producing a polyhydroxyalkanoate, comprising:

(a) maintaining a culture solution at 40° C. to 80° C., wherein the culture solution comprises microbial cells containing a polyhydroxyalkanoate, wherein the microbial cells are of a microorganism selected from the group consisting of *Bacillus megaterium, Cupriavidus necator, Ralstonia eutropha, Alcaligenes latus, Alcaligenes eutrophus*, and *Aeromonas caviae;*

(b) adding an oxidizer to the culture solution obtained in (a), adjusting a pH of the culture solution to from 10.5 to 13.0, and maintaining the culture solution at 30° C. to 75° C., wherein the oxidizer is hydrogen peroxide solution or/and ozone; and (c) adding an enzyme to the aqueous suspension obtained in (b) to subject the microbial cells to enzymatic treatment, wherein the enzyme in (c) is a lytic enzyme and/or an alkaline proteolytic enzyme.

2. The method of claim 1, further comprising:

(d) adding a surfactant and an aqueous alkaline solution to the aqueous suspension obtained in (c) to adjust a pH of the aqueous suspension to from 10.0 to 12.0.

3. The method of claim 1, wherein the polyhydroxyalkanoate in the culture solution obtained in (a) has a weight average molecular weight of from 1,500,000 to 2,500,000; and the culture solution obtained in (a) has a solid content concentration of from 20% by weight to 40% by weight.

4. The method of claim 1, wherein (b) comprises maintaining, for from 0.1 hours to 30 hours, the pH which has been adjusted.

5. The method of claim 1, wherein the polyhydroxyalkanoate in the aqueous suspension obtained in (b) has a weight average molecular weight of from 100,000 to 800,000; and the aqueous suspension obtained in (b) has a solid content concentration of from 20% by weight to 40% by weight.

6. The method of claim 1, wherein, in (b), in a case where hydrogen peroxide is added to the culture solution, the hydrogen peroxide is added such that a concentration of the hydrogen peroxide in the culture solution is from 0.2% by weight to 30% by weight.

7. The method of claim 1, wherein (c) comprises adding a surfactant.

8. The method of claim 2, wherein the surfactant is an anionic surfactant, a cationic surfactant, an amphoteric surfactant, or a nonionic surfactant.

9. The method of claim 2, wherein the surfactant is an anionic surfactant.

10. The method of claim 2, wherein the microorganism is *Cupriavidus necator.*

11. The method of claim 1, wherein the microorganism is *Cupriavidus necator.*

12. The method of claim 4, wherein the microorganism is *Cupriavidus necator.*

13. The method of claim 2, wherein the surfactant is sodium dodecyl sulfate.

* * * * *